(12) United States Patent
Schankel et al.

(10) Patent No.: US 10,292,912 B2
(45) Date of Patent: May 21, 2019

(54) PERSONAL CARE COMPOSITIONS

(71) Applicant: Colgate-Palmolive Company, New York, NY (US)

(72) Inventors: Daniel Schankel, North Brunswick, NJ (US); Shiri Nawrocki, Tenafly, NJ (US); Viktor Dubovoy, Cresskill, NJ (US); Long Pan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/391,830

(22) Filed: Dec. 27, 2016

(65) Prior Publication Data

US 2017/0189285 A1    Jul. 6, 2017

Related U.S. Application Data

(60) Provisional application No. 62/273,315, filed on Dec. 30, 2015.

(51) Int. Cl.
*A61K 8/21* (2006.01)
*A61K 8/19* (2006.01)
*A61K 8/24* (2006.01)
*A61Q 15/00* (2006.01)

(52) U.S. Cl.
CPC .................. *A61K 8/21* (2013.01); *A61K 8/19* (2013.01); *A61K 8/24* (2013.01); *A61Q 15/00* (2013.01); *A61K 2800/30* (2013.01); *A61K 2800/58* (2013.01)

(58) Field of Classification Search
None
See application file for complete search history.

(56) References Cited

U.S. PATENT DOCUMENTS

| | | | |
|---|---|---|---|
| 2,145,583 A | 1/1939 | Carlson | |
| 2,236,387 A | 3/1941 | Wallace et al. | |
| 2,412,535 A * | 12/1946 | Richardson | A61K 8/26 424/68 |
| 2,876,166 A | 3/1959 | Nebergall | |
| 3,028,216 A | 4/1962 | Gemmell et al. | |
| 3,934,004 A | 1/1976 | Orren | |
| 4,071,615 A | 1/1978 | Barth | |
| 4,198,394 A | 4/1980 | Faunce | |
| 4,292,306 A | 9/1981 | Faunce | |

(Continued)

FOREIGN PATENT DOCUMENTS

| | | |
|---|---|---|
| EP | 2 057 978 A1 | 5/2009 |
| EP | 2 289 482 A2 | 3/2011 |

(Continued)

OTHER PUBLICATIONS

National Research Council (US) Subcommittee on Flame-Retardant Chemicals. Washington (DC): National Academies Press (US); 2000, p. 1 (excerpted part only). (Year: 2000).*

(Continued)

*Primary Examiner* — Ernst V Arnold
*Assistant Examiner* — Kyung S Chang

(57) ABSTRACT

Described herein, are aqueous soluble tin phosphate complexes formed from a mixture comprising tin (II) fluoride and a pyrophosphate salt. Also described are external personal care compositions comprising the complexes, and uses thereof.

21 Claims, 7 Drawing Sheets

(56) References Cited

U.S. PATENT DOCUMENTS

| | | | |
|---|---|---|---|
| 4,340,583 A | 7/1982 | Wason | |
| 4,350,680 A | 9/1982 | Harvey et al. | |
| 4,627,977 A | 12/1986 | Gaffar et al. | |
| 4,961,924 A | 10/1990 | Suhonen | |
| 5,000,944 A | 3/1991 | Prencipe et al. | |
| 5,004,597 A | 4/1991 | Majeti et al. | |
| 5,017,363 A | 5/1991 | Subonen | |
| 5,145,666 A | 9/1992 | Lukacovic et al. | |
| 5,188,820 A | 2/1993 | Cummins et al. | |
| 5,213,790 A | 5/1993 | Lukacovic et al. | |
| 5,258,173 A | 11/1993 | Waterfield | |
| 5,281,410 A | 1/1994 | Lukacovic et al. | |
| 5,281,411 A | 1/1994 | Majeti et al. | |
| 5,338,537 A | 8/1994 | White, Jr. et al. | |
| 5,487,906 A | 1/1996 | Dixit et al. | |
| 5,578,293 A | 11/1996 | Prencipe et al. | |
| 5,599,527 A | 2/1997 | Hsu et al. | |
| 5,703,959 A | 12/1997 | Asano et al. | |
| 5,716,600 A | 2/1998 | Zahradnik et al. | |
| 5,939,051 A | 8/1999 | Santalucia et al. | |
| 5,939,052 A | 8/1999 | White, Jr. et al. | |
| 6,187,295 B1 | 2/2001 | Glandorf | |
| 6,190,644 B1 | 2/2001 | McClanahan et al. | |
| 6,350,436 B1 | 2/2002 | Glandorf et al. | |
| 6,455,076 B1 * | 9/2002 | Hahn | A61K 8/19 424/401 |
| 6,464,963 B1 | 10/2002 | Gambogi et al. | |
| 6,555,094 B1 | 4/2003 | Glandorf et al. | |
| 6,652,841 B1 | 11/2003 | Brown et al. | |
| 6,685,920 B2 | 2/2004 | Baig et al. | |
| 6,696,045 B2 | 2/2004 | Yue et al. | |
| 6,713,049 B1 | 3/2004 | White, Jr. et al. | |
| 6,740,311 B2 | 5/2004 | White, Jr. et al. | |
| 6,821,507 B2 | 11/2004 | Glandorf et al. | |
| 7,387,774 B2 | 6/2008 | Faller et al. | |
| 8,211,409 B2 | 7/2012 | Baig et al. | |
| 8,283,135 B2 | 10/2012 | Doyle et al. | |
| 8,481,004 B2 | 7/2013 | Brown et al. | |
| 8,628,755 B2 | 1/2014 | Prencipe | |
| 8,906,347 B2 | 12/2014 | Strand et al. | |
| 8,940,280 B2 | 1/2015 | Brown et al. | |
| 8,956,593 B2 | 2/2015 | Burgess et al. | |
| 9,017,647 B2 | 4/2015 | Midha et al. | |
| 9,139,731 B2 | 9/2015 | Baig et al. | |
| 2004/0042978 A1 | 3/2004 | Embro | |
| 2005/0112070 A1 | 5/2005 | Glandorf et al. | |
| 2006/0141072 A1 | 6/2006 | Arvanitidou et al. | |
| 2007/0025928 A1 | 2/2007 | Glandorf et al. | |
| 2007/0183989 A1 | 8/2007 | Prencipe et al. | |
| 2008/0286214 A1 | 11/2008 | Brown et al. | |
| 2012/0207686 A1 | 8/2012 | Fruge et al. | |
| 2013/0017158 A1 | 1/2013 | Hoke, II et al. | |
| 2013/0216485 A1 | 8/2013 | Campbell et al. | |

FOREIGN PATENT DOCUMENTS

| | | |
|---|---|---|
| WO | WO 98/22079 A1 | 5/1998 |
| WO | WO 01/34108 A1 | 5/2001 |
| WO | WO 02/02128 A2 | 1/2002 |
| WO | WO 03/000217 A2 | 1/2003 |
| WO | WO 03/045344 A2 | 6/2003 |
| WO | WO 2004/054531 A1 | 7/2004 |
| WO | WO 2004/071321 A2 | 8/2004 |
| WO | WO 2007/062365 A2 | 5/2007 |
| WO | WO 2011/053291 A1 | 5/2011 |
| WO | WO 2012/060837 A1 | 5/2012 |
| WO | WO 2012/087288 A2 | 6/2012 |
| WO | WO 2012/166142 A1 | 12/2012 |
| WO | WO 2013/007018 A1 | 1/2013 |
| WO | WO 2013/033090 A1 | 3/2013 |
| WO | WO 2015/028096 A1 | 3/2015 |
| WO | WO 2015/195139 A1 | 12/2015 |
| WO | WO 2015/195140 A1 | 12/2015 |
| WO | WO 2016/105438 | 6/2016 |
| WO | WO 2016/178652 | 11/2016 |

OTHER PUBLICATIONS

The International Search Report and the Written Opinion of the International Searching Authority issued in International Application PCT/US2016/068769 dated Apr. 10, 2017.

Buchner, M. et al., "Pyrophosphate Complex of Tin(II) in Aqueous Solutions as Applied in Electrolytes for the Deposition of Tin and Tin Alloys Such as White Bronze," Inorganic Chemistry, 2012, 51, 8860-8867.

Crest Pro Health Toothpastes, 2 pages, retrieved Dec. 30, 2015, from http://www.pgsdscpsia.com/productsafety/ingredients/Crest_Pro_Health_Toothpastes.pdf.

Donaldson, J., "The Chemistry of Bivalent Tin," in Progress in Inorganic Chemistry, Cotton, F., Ed., 1967, John Wiley & Sons, Inc., pp. 287-356.

Safety Data Sheet for Crest Pro-Health Clean Cinnamon, face of document states Issuing Date: Apr. 2, 2015 and Revision Date: Apr. 2, 2015, 6 pages, retrieved Dec. 30, 2015, from: http://www.pg.com/productsafety/sds/SDS_2015/Crest%20Pro-Health%20Clean%20Cinnamon-95399027_RET_NG-2015040210392.pdf.

Safety Data Sheet for Crest Pro-Health Clean Mint Toothpaste, face of document states Issuing Date: Apr. 2, 2015 and Revision Date: Aug. 13, 2015, 8 pages, retrieved Dec. 30, 2015, from http://www.pg.com/productsafety/sds/SDS_2015/SDS_Dec_2015/Crest_ProHealth_Clean_Mint_Toothpaste_95113822_RET_NG_2015081310209.pdf.

Safety Data Sheet for Crest Pro-Health for Life-Smooth Mint, face of document states: Issuing Date: Apr. 2, 2015 and Revistion Date: Apr. 2, 2015, 6 pages, retrieved Dec. 30, 2015, from http://www.pg.com/productsafety/sds/SDS_2015/Crest%20Pro-Health%20For%20Life-%20Smooth%20Mint-98941394_RET_NG-2015040291917.pdf.

Safety Data Sheet for Crest Pro-Health for Life-Smooth Mint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20For%20Life-%20Smooth%20Mint-98941394_RET_NG-2015040244324.pdf.

Safety Data Sheet for Crest Pro-Health Clean Mint Toothpaste, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Clean%20Mint%20Toothpaste-95113822_RET_NG-2015040210190.pdf.

Safety Data Sheet for Crest Pro-Health Intensive Clean-Cool Mint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Intensive%20Clean%20-%20Cool%20Mint-95720693_RET_NG-201504029280.pdf.

Safety Data Sheet for Crest Pro-Health Intensive Clean-Cool Mint, face of document states Issuing Date: Apr. 2, 2015 and Revision Date: Jun. 29, 2015, 8 pages, retrieved Dec. 30, 2015, from http://www.pg.com/productsafety/sds/SDS_2015/SDS_Dec_2015/Crest_ProHealth_Intensive_Clean_Cool_Mint_95720693_RET_NG_2015102211039.pdf.

Safety Data Sheet for Crest Pro-Health Intensive Clean-Cool Mint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Intensive%20Clean%20-%20Cool%20Mint-95720693_RET_NG-2015040272630.pdf.

Safety Data Sheet for Crest Pro-Health Whitening—Fresh Clean Mint, face of dcoument states Issuing Date: Apr. 8, 2015 and Revision Date: Apr. 8, 2015, 7 pages, retrieved Dec. 30, 2015, from http://www.pg.com/productsafety/sds/SDS_2015/Crest%20Pro-Health%20Whitening%20-Fresh%20Clean%20Mint-98543475_RET_NG-2015040845158.pdf.

(56) References Cited

OTHER PUBLICATIONS

Safety Data Sheet for Crest Pro-Health Healthy Fresh-Cool Peppermint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Healthy%20Fresh-%20Cool%20Peppermint-92090509_RET_NG-20150402750.pdf.

Safety Data Sheet for Crest Pro-Health Healthy Fresh-Cool Peppermint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Healthy%20Fresh-%20Cool%20Peppermint-92090509_RET_NG-2015040292539.pdf.

Safety Data Sheet for Crest Pro-Health Clinical Plaque Control—Fresh Mint, face of document states Issuing Date: No data available and Revision Date: Aug. 13, 2015, 8 pages, retrieved Dec. 30, 2015, from http://www.pg.com/productsafety/sds/SDS_2015/SDS_Dec_2015/Crest_ProHealth-Clinical_Plaque_Control_Fresh_Mint_9867882_RET_NG_2015081311225.pdf.

Safety Data Sheet for Crest Pro-Health Sensitive + Enamel Sheild—Smooth Mint, face a document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Sensitive%20+%20Enamel%20Sheild-%20Smooth%20Mint-95931348_RET_NG-201504029300.pdf.

Safety Data Sheet for Crest Pro-Health Clinical Plaque Control—Fresh Mint, face of document states Issuing Date: No data available and Revision Date: Apr. 2, 2015, 6 pages, retrieved Dec. 30, 2015, from http://www.pg.com/productsafety/sds/SDS_2015/Crest%20Pro-Health%20Clinical%20Plaque%20Control%20-%20Fresh%20Mint-99867882_RET_NG-201540295522.pdf.

Safety Data Sheet for Crest Pro-Health Sensitive + Enamel Sheild—Smooth Mint, face of document states Issuing Date: Apr. 2, 2015 and Revision Date: Apr. 2, 2015, 6 pages, retrieved Dec. 30, 2015, from http://www.pg.com/productsafety/sds/SDS_2015/Crest%20Pro-Health%20Sensitive%20+%20Enamel%20Sheild-%20Smooth%20Mint-95931348_RET_NG-2015040210328.pdf.

Safety Data Sheet for Crest Pro-health Clinical Gum Protection—Soothing Smooth Mint, face of document states Issuing Date: Apr. 2, 2015 and Revision Date: Apr. 2, 2015, 7 pages, retrieved Dec. 30, 2015, from http://www.pg.com/productsafety/sds/SDS_2015/Crest%20Pro-Health%20Clinical%20Gum%20Protection%20-%20Soothing%20Smooth%20Mint-98854209_RET_NG-201504029519.pdf.

Safety Data Sheet for Crest Pro-Health Clinical Gum Protection—Soothing Smooth Mint, face of document states Issuing Date: Apr. 2, 2015 and Revision Date: Aug. 13, 2015, 8 pages, retrieved Dec. 30, 2015, from http://www.pg.com/productsafety/sds/SDS_2015/SDS_Dec_2015/Crest_ProHealth-Clinical_Gum_Protection_Soothing_Smooth_Mint_98854209_RET_NG_20150813113638.pdf.

Safety Data Sheet for Crest Pro-Health Clinical Gum Protection—Invigorating Clean Mint, face of document states Issuing Date: No data available and Revision Date: Aug. 13, 2015, 8 pages, retrieved Dec. 30, 2015, from http://www.pg.com/productsafety/sds/SDS_2015/SDS_Dec_2015/Crest_ProHealth_Clinical_Gum_Protection_Invigorating_Clean_Mint_99543035_RET_NG_20150813114619.pdf.

Safety Data Sheet for Crest Pro-Health [HD] Step 1 Fluoride Toothpaste for Anti-Cavity and Anti-Gingivitis, face of document states Issuing Date: Apr. 14, 2015 and Revision Date: Apr. 14, 2015, 6 pages, retrieved Dec. 30, 2015, from http://www.pg.com/productsafety/sds/SDS_2015/Crest%20Pro-Health%20%5BHD%5D%20Step%201%20Fluoride%20Toothpaste%20for%20Anti-Cavity%20and%20Anti-Gigivitis-97263583_RET_NG-201504146928.pdf.

* cited by examiner

PERSONAL CARE COMPOSITIONS

This application claims priority to U.S. Provisional Application No. 62/273,315 filed Dec. 30, 2015, which is hereby incorporated by reference in its entirety.

BACKGROUND

There have been many antiperspirants designed to help people reduce sweat. Examples of these can be found in U.S. Code of Regulation 21 C.F.R. § 350. The majority of the active agents used in antiperspirants are aluminum and zirconium halide compounds and complexes and their derivatives. While these active agents are generally effective, there is still a need for alternative antiperspirant actives.

Tin (II) fluoride (also known as stannous fluoride) is soluble in water, however, it oxidizes to form insoluble precipitates of tin. In addition, tin can form insoluble compounds with phosphates. Thus, there is still a need for methods to stabilize tin (II) fluoride to make it effective in personal care products. Embodiments of the present invention are designed to meet these, and other, needs.

BRIEF SUMMARY

It has now been discovered that tin (II) fluoride forms an aqueous soluble tin phosphate complex upon mixture with a pyrophosphate salt, e.g., tetrapotassium pyrophosphate ($K_4P_2O_7$) (TKPP) or tetrasodium pyrophosphate ($Na_4P_2O_7$) (TSPP). In contrast, tin (II) chloride upon mixture with a pyrophosphate salt, e.g., tetrapotassium pyrophosphate ($K_4P_2O_7$) (TKPP) or tetrasodium pyrophosphate ($Na_4P_2O_7$) (TSPP), forms solid (Examples 8 and 9).

Without being bound by theory, it is believed that when the complex is contacted with proteins to simulate sweat, the aqueous soluble tin phosphate complex forms a white precipitate, which may be an appropriate occlusive active for wetness control because it forms plugs that can physically inhibit sweat from skin.

Provided is an aqueous soluble tin phosphate complex, e.g., formed from a mixture comprising tin (II) fluoride and a pyrophosphate salt, e.g., an alkali pyrophosphate salt, e.g., tetrapotassium pyrophosphate ($K_4P_2O_7$) (TKPP) or tetrasodium pyrophosphate ($Na_4P_2O_7$) (TSPP).

Also provided are external personal care compositions, e.g., antiperspirants and/or deodorants, comprising the aqueous soluble tin phosphate complex.

Further provided are antiperspirants and/or deodorants comprising the aqueous soluble tin phosphate complex that form a precipitate when contacted with sweat.

Further provided are external personal care compositions, e.g., antiperspirants and/or deodorants, comprising tin (II) fluoride and a pyrophosphate salt, e.g., an alkali pyrophosphate salt, e.g., tetrapotassium pyrophosphate ($K_4P_2O_7$) (TKPP) or tetrasodium pyrophosphate ($Na_4P_2O_7$) (TSPP), e.g., tetrapotassium pyrophosphate ($K_4P_2O_7$), e.g., tetrasodium pyrophosphate ($Na_4P_2O_7$) (TSPP), wherein the tin (II) fluoride and pyrophosphate salt form an aqueous soluble tin phosphate complex.

Further provided are methods of using the external personal care compositions, e.g., antiperspirants, to occlude pores and/or reduce sweat in a person in need thereof comprising applying the composition to the skin of the person.

Further provided are methods of making the aqueous soluble tin phosphate complex comprising combining tin (II) fluoride and a pyrophosphate salt, e.g., an alkali pyrophosphate salt, e.g., tetrapotassium pyrophosphate ($K_4P_2O_7$) (TKPP) or tetrasodium pyrophosphate ($Na_4P_2O_7$) (TSPP), in aqueous solution, e.g., at a molar ratio of at least 1P:1Sn, e.g., 1P:1 Sn to 15P:1Sn, e.g., 1P:1Sn to less than 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., P:1Sn to 2P:1Sn, e.g., 1P:1Sn, e.g., 2P:1Sn, e.g., 5P:1Sn, e.g., 10P:1Sn, e.g., 15P:1Sn; optionally isolating the complex thus formed as a solid.

Further provided are methods of making the external personal care compositions, e.g., antiperspirants, comprising admixing the aqueous soluble tin phosphate complex with a personal care carrier.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
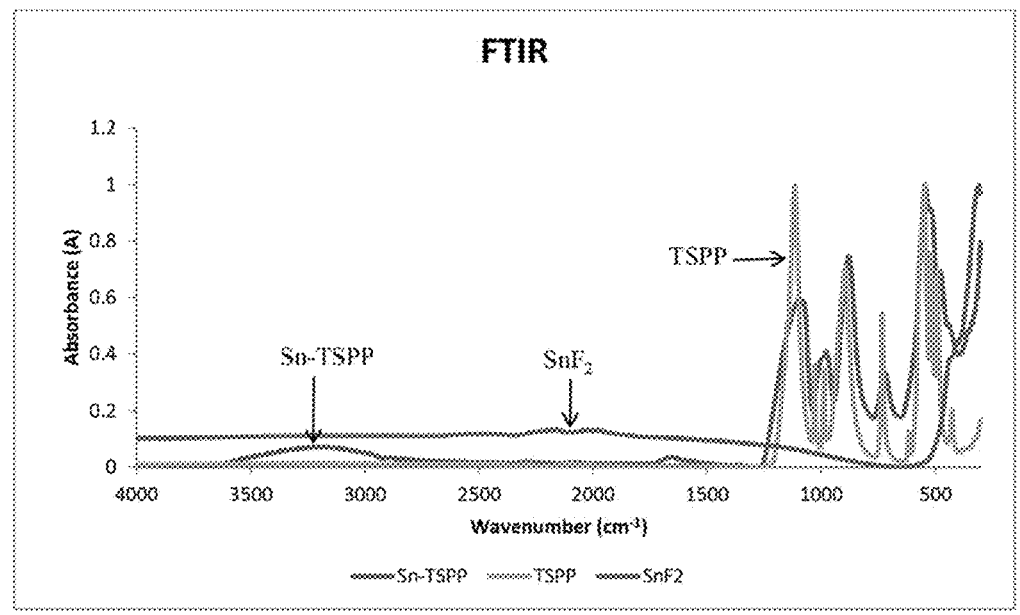
FIG. 1 depicts Fourier transform infrared spectra.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Provided is an aqueous soluble tin phosphate complex (Complex 1), e.g., 1.1 Complex 1, wherein the complex is formed from a mixture comprising tin (II) fluoride and a pyrophosphate salt, e.g., an alkali pyrophosphate salt, e.g., tetrapotassium pyrophosphate or tetrasodium pyrophosphate.

1.2 Complex 1 or 1.1, wherein the complex is formed from a mixture comprising tin (II) fluoride and a pyrophosphate salt, e.g., an alkali pyrophosphate salt, e.g., tetrapotassium pyrophosphate or tetrasodium pyrophosphate, in an aqueous solution.

1.3 Complex 1.2, wherein the aqueous solution has a pH from 5-11, e.g., 5-10, e.g., 5-9, e.g., 5-8, e.g., 5-7, e.g., 5-6, e.g., 6-8, e.g., 6-7, e.g., 8-9, e.g., 9-10, e.g., 10-11. Complex 1.2, wherein the pyrophosphate salt is tetrapotassium pyrophosphate and the aqueous solution has a pH from 5-11, e.g., 5-10, e.g., 5-9, e.g., 5-8, e.g., 5-7, e.g., 5-6, e.g., 6-8, e.g., 6-7, e.g., 9-10, e.g., 10-11. Complex 1.2, wherein the pyrophosphate salt is tetrasodium pyrophosphate and the aqueous solution has a pH from 5-9, e.g., 5-8, e.g., 5-7, e.g., 5-6, e.g., 6-8, e.g., 6-7, e.g., 8-9.

1.4 Any of the foregoing complexes, wherein the complex is formed from a mixture comprising the tin (II) fluoride and pyrophosphate salt in a molar ratio of at least 1P:1Sn, e.g., 1P:1Sn to 15P:1Sn, e.g., 1P:1Sn to less than 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn. e.g., 1P:1Sn, e.g., 2P:1Sn, e.g., 5P:1Sn, e.g., 10P:1Sn, e.g., 15P:1Sn.

1.5 Any of the foregoing complexes, wherein the complex is formed from a mixture comprising the tin (II) fluoride and pyrophosphate salt in a molar ratio of 1P:1Sn to 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

1.6 Any of the foregoing complexes, wherein the complex is formed from a mixture comprising 1-10 weight % tin (II) fluoride by weight of the mixture, e.g., 1-9 weight % tin (II) fluoride by weight of the mixture, e.g., 2 weight % tin (II) fluoride by weight of the mixture, and 1-40 weight % pyrophosphate salt by weight of the mixture, e.g., 1-30 weight % pyrophosphate salt by weight of the mixture, e.g., 1-20 weight % pyrophosphate salt by weight of the mixture, e.g., 1-10 weight % pyrophosphate salt by weight of the mixture.

1.7 Any of the foregoing complexes, wherein the complex is formed from a mixture comprising tin (II) fluoride and tetrapotassium pyrophosphate ($K_4P_2O_7$) (TKPP).

1.8 Complex 1.7, wherein the complex is formed from a mixture comprising tin (II) fluoride and tetrapotassium pyrophosphate ($K_4P_2O_7$) (TKPP) in a molar ratio of at least 1P:1Sn, e.g., 1P:1Sn to 15P:1Sn, e.g., 1P:1Sn to less than 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

1.9 Complex 1.7 or 1.8, wherein the complex is formed from a mixture comprising 1-10 weight % tin (II) fluoride by weight of the mixture, e.g., 1-9 weight % tin (II) fluoride by weight of the mixture, e.g., 2 weight % tin (II) fluoride by weight of the mixture, and 1-40 weight % tetrapotassium pyrophosphate by weight of the mixture, e.g., 1-30 weight % tetrapotassium pyrophosphate by weight of the mixture, e.g., 1-20 weight % tetrapotassium pyrophosphate by weight of the mixture, e.g., 1-10 weight % tetrapotassium pyrophosphate by weight of the mixture.

1.10 Any of Complex 1 or 1.1-1.6, wherein the complex is formed from a mixture comprising tin (II) fluoride and tetrasodium pyrophosphate.

1.11 Complex 1.10, wherein the complex is formed from a mixture comprising tin (II) fluoride and tetrasodium pyrophosphate in a molar ratio of 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:1Sn, e.g., 5P:1Sn.

1.12 Complex 1.10 or 1.11, wherein the complex is formed from a mixture comprising 1-10 weight % tin (II) fluoride by weight of the mixture, e.g., 1-9 weight % tin (II) fluoride by weight of the mixture, e.g., 2 weight % tin (II) fluoride by weight of the mixture, and 1-30 weight % tetrasodium pyrophosphate by weight of the mixture, e.g., 1-20 weight % tetrasodium pyrophosphate by weight of the mixture, e.g., 1-10 weight % tetrasodium pyrophosphate by weight of the mixture.

1.13 Any of the foregoing complexes, wherein the complex exhibits a Fourier transform infrared spectrum substantially as shown in the Sn-TSPP spectrum in FIG. 1.

Figure 2:
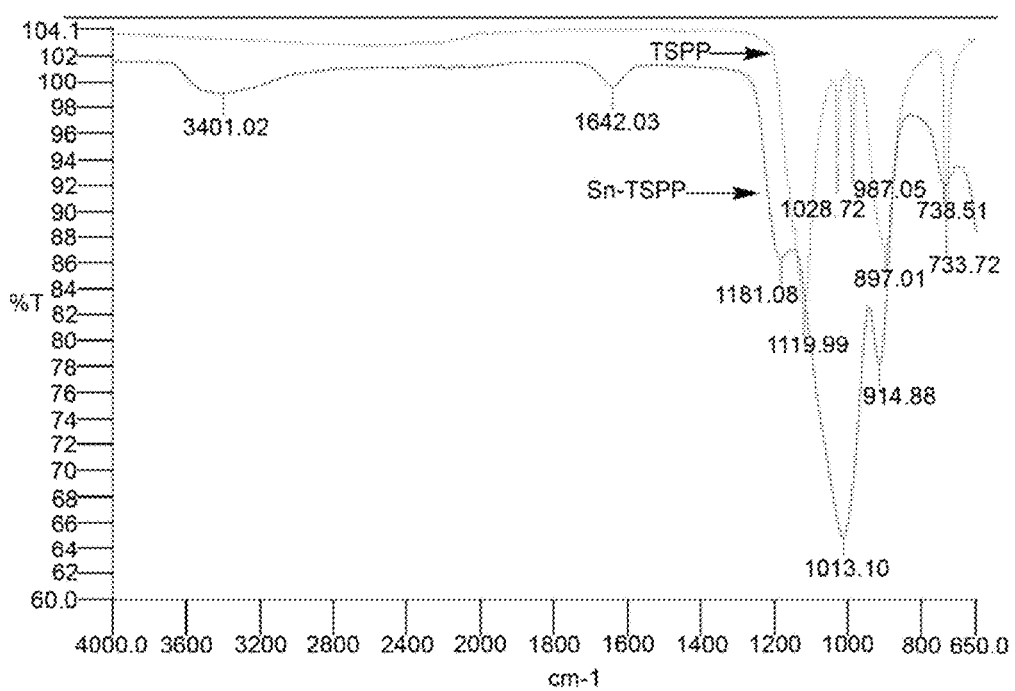
FIG. 2 depicts Fourier transform infrared spectra.

1.14 Any of the foregoing complexes, wherein the complex exhibits a Fourier transform infrared spectrum substantially as shown in the Sn-TSPP spectrum in FIG. 2.

1.15 Any of the foregoing complexes, wherein the complex exhibits a Fourier transform infrared spectrum comprising one or more peaks selected from the group consisting of: 1181 $cm^{-1}$, 1013 $cm^{-1}$, 915 $cm^{-1}$, and 739 $cm^{-1}$.

1.16 Any of the foregoing complexes, wherein the complex exhibits a Fourier transform infrared spectrum comprising one or more peaks selected from the group consisting of: 3401 $cm^{-1}$, 1642 $cm^{-1}$, 1181 $cm^{-1}$, 1013 $cm^{-1}$, 915 $cm^{-1}$, and 739 $cm^{-1}$.

1.17 Any of the foregoing complexes, wherein the complex exhibits a Fourier transform infrared spectrum comprising the following peaks: 1181 $cm^{-1}$, 1013 $cm^{-1}$, 915 $cm^{-1}$, and 739 $cm^{-1}$.

1.18 Any of the foregoing complexes, wherein the complex exhibits a Fourier transform infrared spectrum comprising the following peaks: 3401 $cm^{-1}$, 1642 $cm^{-1}$, 1181 $cm^{-1}$, 1013 $cm^{-1}$, 915 $cm^{-1}$, and 739 $cm^{-1}$.

1.19 Any of the foregoing complexes, wherein the complex exhibits a Fourier transform infrared spectrum comprising one or more peaks selected from the group consisting of: 1101 $cm^{-1}$, 1081 $cm^{-1}$, 979 $cm^{-1}$, 722 $cm^{-1}$, 546 $cm^{-1}$, and 481 $cm^{-1}$.

1.20 Any of the foregoing complexes, wherein the complex exhibits a Fourier transform infrared spectrum comprising the following peaks: 1101 $cm^{-1}$, 1081 $cm^{-1}$, 979 $cm^{-1}$, 722 $cm^{-1}$, 546 $cm^{-1}$, and 481 $cm^{-1}$.

1.21 Any of the foregoing complexes, wherein the complex exhibits a Fourier transform infrared spectrum comprising one or more peaks selected from the group consisting of: 1101 $cm^{-1}$, 1081 $cm^{-1}$, 979 $cm^{-1}$, 881 $cm^{-1}$, 722 $cm^{-1}$, 546 $cm^{-1}$, and 481 $cm^{-1}$.

1.22 Any of the foregoing complexes, wherein the complex exhibits a Fourier transform infrared spectrum comprising the following peaks: 1101 $cm^{-1}$, 1081 $cm^{-1}$, 979 $cm^{-1}$, 881 $cm^{-1}$, 722 $cm^{-1}$, 546 $cm^{-1}$, and 481 $cm^{-1}$.

Figure 6:
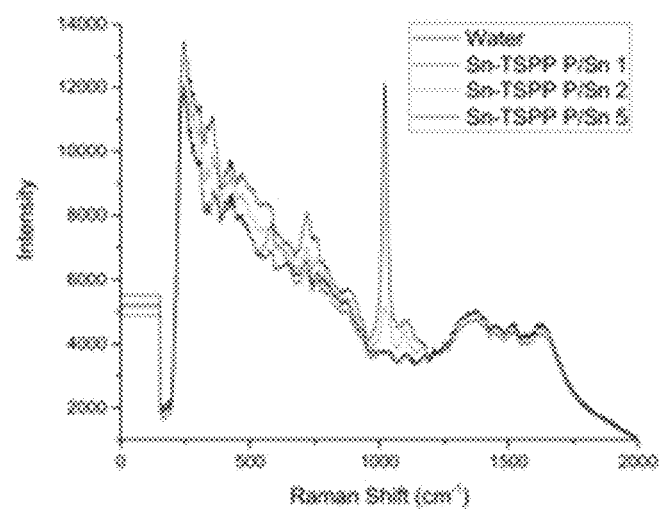
FIG. 6 depicts Raman spectra of water and solutions with P:Sn molar ratios of 1, 2, and 5 (from top to bottom: P:Sn molar ratio 5, P:Sn molar ratio 2, P:Sn molar ratio 1, and water).

1.23 Any of the foregoing complexes, wherein the complex exhibits a Raman spectrum substantially as shown in any of the P/Sn Raman spectra of FIG. 6.

1.24 Any of the foregoing complexes, wherein the complex exhibits a Raman spectrum comprising a peak at 1022 $cm^{-1}$.

Figure 3:
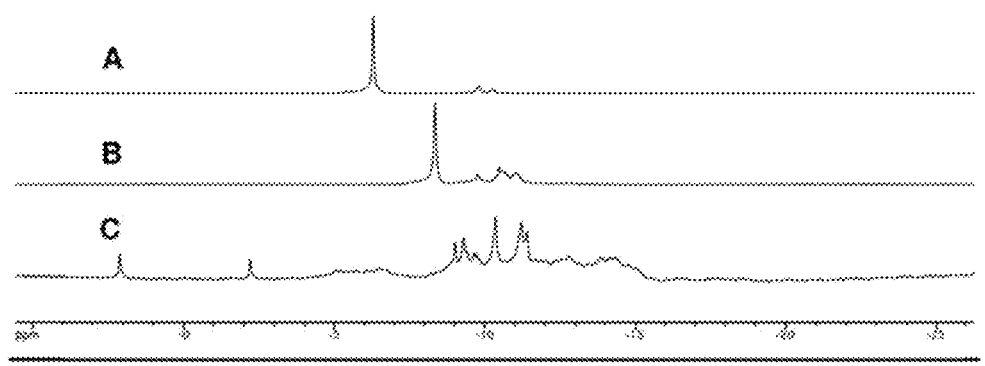
FIGS. 3a, 3b, and 3c depict $^{31}$P NMR spectra of solutions with P:Sn molar ratios of 5 (FIG. 3a), 2 (FIG. 3b), and 1 (FIG. 3c).

1.25 Any of the foregoing complexes, wherein the complex exhibits a $^{31}$P NMR spectrum as shown in any of the NMR spectra of FIG. 3a, 3b, or 3c, wherein the NMR spectrum is obtained on an aqueous solution with 5 weight % D$_2$O added and is externally referenced to 85% H$_3$PO$_4$ set to 0 ppm.

1.26 Any of the foregoing complexes, wherein the complex exhibits a $^{31}$P NMR spectrum comprising the following peak: −6 ppm, e.g., −6.3 ppm, e.g., −6.30 ppm, wherein the NMR spectrum is obtained on an aqueous solution with 5 weight % D$_2$O added and is externally referenced to 85% H$_3$PO$_4$ set to 0 ppm.

1.27 Any of the foregoing complexes, wherein the complex exhibits a $^{31}$P NMR spectrum comprising one or more peaks selected from the group consisting of: −6 ppm, −10 ppm, and −10 ppm (doublet), e.g., −6.3 ppm, −9.8 ppm, −10.2 ppm (doublet), and −10.3 ppm (doublet), e.g., −6.30 ppm, −9.82 ppm, −10.23 ppm (doublet), and −10.31 ppm (doublet), wherein the NMR spectrum is obtained on an aqueous solution with 5 weight % D$_2$O added and is externally referenced to 85% H$_3$PO$_4$ set to 0 ppm.

1.28 Any of the foregoing complexes, wherein the complex exhibits a $^{31}$P NMR spectrum comprising the following peaks: −6 ppm, −10 ppm, and −10 ppm (doublet), e.g., −6.3 ppm, −9.8 ppm, −10.2 ppm (doublet), and −10.3 ppm (doublet), e.g., −6.30 ppm, −9.82 ppm, −10.23 ppm (doublet), and −10.31 ppm (doublet), wherein the NMR spectrum is obtained on an aqueous solution with 5 weight % D$_2$O added and is externally referenced to 85% H$_3$PO$_4$ set to 0 ppm.

1.29 Any of the foregoing complexes, wherein the complex exhibits a $^{31}$P NMR spectrum comprising the following peak: −8 ppm, e.g., −8.3 ppm, e.g., −8.34 ppm, wherein the NMR spectrum is obtained on an aqueous solution with 5 weight % D$_2$O added and is externally referenced to 85% H$_3$PO$_4$ set to 0 ppm.

1.30 Any of the foregoing complexes, wherein the complex exhibits a $^{31}$P NMR spectrum comprising one or more peaks selected from the group consisting of: −8 ppm, −10 ppm, and −11 ppm, e.g., −8.3 ppm, −9.8 ppm, −10.5 ppm, −10.7 ppm, and −11.1 ppm, e.g., −8.34 ppm, −9.78 ppm, −10.49 ppm, −10.69 ppm, and −11.09 ppm, wherein the NMR spectrum is obtained on an aqueous solution with 5 weight % D$_2$O added and is externally referenced to 85% H$_3$PO$_4$ set to 0 ppm.

1.31 Any of the foregoing complexes, wherein the complex exhibits a $^{31}$P NMR spectrum comprising the following peaks: −8 ppm, −10 ppm, and −11 ppm, e.g., −8.3 ppm, −9.8 ppm, −10.5 ppm, −10.7 ppm, and −11.1 ppm, e.g., −8.34 ppm, −9.78 ppm, −10.49 ppm, −10.69 ppm, and −11.09 ppm, wherein the NMR spectrum is obtained on an aqueous solution with 5 weight % D$_2$O added and is externally referenced to 85% H$_3$PO$_4$ set to 0 ppm.

1.32 Any of the foregoing complexes, wherein the complex exhibits a $^{31}$P NMR spectrum comprising one or more peaks selected from the group consisting of: 2 ppm, −9 ppm, −10 ppm, −11 ppm, −13 ppm, and −14 ppm, e.g., 2.1 ppm, 2.2 ppm, −9.0 ppm, −9.3 ppm, −9.7 ppm, −10.4 ppm, −11.2 ppm, −11.4 ppm, −12.8 ppm, and −14.4 ppm, e.g., 2.10 ppm, 2.22 ppm, −9.03 ppm, −9.31 ppm, −9.65 ppm, −9.74 ppm, −10.36 ppm, −11.22 ppm, −11.40 ppm, −12.77 ppm, and −14.35 ppm, wherein the NMR spectrum is obtained on an aqueous solution with 5 weight % 120 added and is externally referenced to 85% H$_3$PO$_4$ set to 0 ppm.

1.33 Any of the foregoing complexes, wherein the complex exhibits a $^{31}$P NMR spectrum comprising the following peaks: 2 ppm, −9 ppm, −10 ppm, −11 ppm, −13 ppm, and −14 ppm, e.g., 2.1 ppm, 2.2 ppm, −9.0 ppm, −9.3 ppm, −9.7 ppm, −10.4 ppm, −11.2 ppm, −11.4 ppm, −12.8 ppm, and −14.4 ppm, e.g., 2.10 ppm, 2.22 ppm, −9.03 ppm, −9.31 ppm, −9.65 ppm, −9.74 ppm, −10.36 ppm, −11.22 ppm, −11.40 ppm, −12.77 ppm, and −14.35 ppm, wherein the NMR spectrum is obtained on an aqueous solution with 5 weight % D$_2$O added and is externally referenced to 85% H$_3$PO$_4$ set to 0 ppm.

Figure 4:
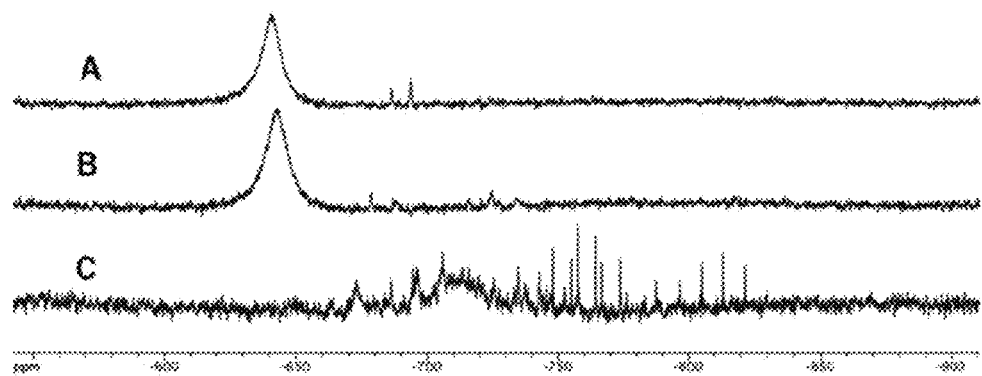
FIGS. 4a, 4b, and 4c depict $^{119}$Sn NMR spectra of solutions with P:Sn molar ratios of 5 (FIG. 4a), 2 (FIG. 4b), and 1 (FIG. 4c).

1.34 Any of the foregoing complexes, wherein the complex exhibits a $^{119}$Sn NMR spectrum as shown in any of the NMR spectra of FIG. 4a, 4b, or 4c, wherein the NMR spectrum is obtained on an aqueous solution with 5 weight % D$_2$O added and is externally referenced to saturated SnF$_2$ in D$_2$O at −796 ppm.

1.35 Any of the foregoing complexes, wherein the complex exhibits a $^{119}$Sn NMR spectrum comprising the following peak: −641 ppm, e.g., −640.6 ppm, e.g., −640.63 ppm, wherein the NMR spectrum is obtained on an aqueous solution with 5 weight % D$_2$O added and is externally referenced to saturated SnF$_2$ at −796 ppm.

1.36 Any of the foregoing complexes, wherein the complex exhibits a $^{119}$Sn NMR spectrum comprising one or more peaks selected from the group consisting of: −641 ppm, −687 ppm, and −694 ppm, e.g., −640.6 ppm, −686.6 ppm, and −693.8 ppm, e.g., −640.63 ppm, −686.58 ppm, and −693.76 ppm, wherein the NMR spectrum is obtained on an aqueous solution with 5 weight % D$_2$O added and is externally referenced to saturated SnF$_2$ at −796 ppm.

1.37 Any of the foregoing complexes, wherein the complex exhibits a $^{119}$Sn NMR spectrum comprising the following peaks: −641 ppm, −687 ppm, and −694 ppm, e.g., −640.6 ppm, −686.6 ppm, and −693.8 ppm, e.g., −640.63 ppm, −686.58 ppm, and −693.76 ppm, wherein the NMR spectrum is obtained on an aqueous solution with 5 weight % D$_2$O added and is externally referenced to saturated SnF$_2$ in D$_2$O at −796 ppm.

1.38 Any of the foregoing complexes, wherein the complex exhibits a $^{119}$Sn NMR spectrum comprising the following peak: −642 ppm, e.g., −642.4 ppm, e.g., −642.35 ppm, wherein the NMR spectrum is obtained on an aqueous solution with 5 weight % D$_2$O added and is externally referenced to saturated SnF$_2$ at −796 ppm.

1.39 Any of the foregoing complexes, wherein the complex exhibits a $^{119}$Sn NMR spectrum comprising one or more peaks selected from the group consisting of: −642 ppm, −679 ppm, and −725 ppm, e.g., −642.4 ppm, −678.8 ppm, and −724.6 ppm, e.g., −642.35 ppm, −678.79 ppm, and −724.61 ppm, wherein the NMR spectrum is obtained on an aqueous solution with 5 weight % D$_2$O added and is externally referenced to saturated SnF$_2$ at −796 ppm.

1.40 Any of the foregoing complexes, wherein the complex exhibits a $^{119}$Sn NMR spectrum comprising the following peaks: −642 ppm, −679 ppm, and −725 ppm, e.g., −642.4 ppm, −678.8 ppm, and −724.6 ppm, e.g., −642.35 ppm, −678.79 ppm, and −724.61 ppm, wherein the NMR spectrum is obtained on an aqueous solution with 5 weight % D$_2$O added and is externally referenced to saturated SnF$_2$ in D$_2$O at −796 ppm.

1.41 Any of the foregoing complexes, wherein the complex exhibits a $^{119}$Sn NMR spectrum comprising one or more peaks selected from the group consisting of: −673 ppm, −686 ppm, −696 ppm, −706 ppm, −735 ppm, −743 ppm, −748 ppm, −755 ppm, −764 ppm, −767 ppm, −774 ppm, −805 ppm, −813 ppm, and −821 ppm, e.g., −673.0 ppm, −686.4 ppm, −696.1 ppm, −705.8 ppm, −734.9 ppm, −742.9 ppm, −747.9 ppm, −755.0 ppm, −764.4 ppm, −766.7 ppm, −773.8 ppm, −804.8 ppm, −813.1 ppm, and −821.5 ppm, e.g., −672.97 ppm, −686.36 ppm, −696.08 ppm, −705.84 ppm, −734.85 ppm, −742.85 ppm, −747.93 ppm, −754.99 ppm, −764.39 ppm, −766.74 ppm, −773.79 ppm, −804.84 ppm, −813.14 ppm, and −821.45 ppm, wherein the NMR spectrum is obtained on an aqueous solution with 5 weight % $D_2O$ added and is externally referenced to saturated $SnF_2$ at −796 ppm.

1.42 Any of the foregoing complexes, wherein the complex exhibits a $^{119}Sn$ NMR spectrum comprising the following peaks: −673 ppm, −686 ppm, −696 ppm, −706 ppm, −735 ppm, −743 ppm, −748 ppm, −755 ppm, −764 ppm, −767 ppm, −774 ppm, −805 ppm, −813 ppm, and −821 ppm, e.g., −673.0 ppm, −686.4 ppm, −696.1 ppm, −705.8 ppm, −734.9 ppm, −742.9 ppm, −747.9 ppm, −755.0 ppm, −764.4 ppm, −766.7 ppm, −773.8 ppm, −804.8 ppm, −813.1 ppm, and −821.5 ppm, e.g., −672.97 ppm, −686.36 ppm, −696.08 ppm, −705.84 ppm, −734.85 ppm, −742.85 ppm, −747.93 ppm, −754.99 ppm, −764.39 ppm, −766.74 ppm, −773.79 ppm, −804.84 ppm, −813.14 ppm, and −821.45 ppm, wherein the NMR spectrum is obtained on an aqueous solution with 5 weight % $D_2O$ added and is externally referenced to saturated $SnF_2$ in $D_2O$ at −796 ppm.

1.43 Any of the foregoing complexes, wherein the complex is $[P_2O_7]^{4-}Na^+Sn^{2+}{}_2F^-$.

1.44 Any of the foregoing complexes, wherein the complex is isolated.

1.45 Any of the foregoing complexes, wherein the complex is lyophilized.

1.46 Any of the foregoing complexes, wherein the complex is isolated with an anti-solvent, e.g., an organic solvent, e.g., ethanol.

1.47 Any of the foregoing complexes for use in an external personal care composition, e.g., an antiperspirant, deodorant, body wash, shower gel, soap (e.g., bar soap, hand soap), shampoo, hair conditioner, or cosmetic, e.g., an antiperspirant and/or deodorant comprising the aqueous soluble tin phosphate complex as described in any of the foregoing, e.g., a body wash or soap (e.g., hand soap) comprising the aqueous soluble tin phosphate complex as described in any of the foregoing.

1.48 Any of the foregoing complexes for use to occlude pores.

1.49 Any of the foregoing complexes for use to reduce sweat.

Further provided is a method (Method 1) to occlude pores and/or reduce sweat, in a person in need thereof comprising applying an effective amount of any of Complex 1 et seq. to the skin of the person.

Further provided is a method (Method 2) of making an aqueous soluble tin phosphate complex, e.g., any of Complex 1 et seq., comprising combining tin (II) fluoride and a pyrophosphate salt, e.g., an alkali pyrophosphate salt, e.g., tetrapotassium pyrophosphate ($K_4P_2O_7$) (TKPP) or tetrasodium pyrophosphate ($Na_4P_2O_7$) (TSPP), e.g., 2.1 Method 2 comprising combining the tin (II) fluoride and pyrophosphate salt, e.g., alkali pyrophosphate salt, in an aqueous solution.

2.2 Method 2.1, wherein the aqueous solution has a pH from 5-11, e.g., 5-10, e.g., 5-9, e.g., 5-8, e.g., 5-7, e.g., 5-6, e.g., 6-8, e.g., 6-7, e.g., 8-9, e.g., 9-10, e.g., 10-11. Method 2.1, wherein the pyrophosphate salt is tetrapotassium pyrophosphate and the aqueous solution has a pH from 5-11, e.g., 5-10, e.g., 5-9, e.g., 5-8, e.g., 5-7, e.g., 5-6, e.g., 6-8, e.g., 6-7, e.g., 9-10, e.g., 10-11. Method 2.1, wherein the pyrophosphate salt is tetrasodium pyrophosphate and the aqueous solution has a pH from 5-9, e.g., 5-8, e.g., 5-7, e.g., 5-6, e.g., 6-8, e.g., 6-7, e.g., 8-9.

2.3 Any of the foregoing methods comprising combining the tin (II) fluoride and pyrophosphate salt in a molar ratio of at least 1P:1Sn, e.g., 1P:1Sn to 15P:1Sn, e.g., 1P:1Sn to less than 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

2.4 Any of the foregoing methods comprising combining the tin (II) fluoride and pyrophosphate salt in a molar ratio of 1P:1Sn to 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

2.5 Any of the foregoing methods comprising combining 1-10 weight % tin (II) fluoride by weight of the combination, e.g., 1-9 weight % tin (II) fluoride by weight of the combination, e.g., 2 weight % tin (II) fluoride by weight of the combination, and 1-40 weight % pyrophosphate salt by weight of the combination, e.g., 1-30 weight % pyrophosphate salt by weight of the combination, e.g., 1-20 weight % pyrophosphate salt by weight of the combination, e.g., 1-10 weight % pyrophosphate salt by weight of the combination.

2.6 Any of the foregoing methods, wherein the pyrophosphate salt is tetrapotassium pyrophosphate ($K_4P_2O_7$).

2.7 Method 2.6 comprising combining the tin (II) fluoride and tetrapotassium pyrophosphate in a molar ratio of at least 1P:1Sn, e.g., 1P:1Sn to 15P:1Sn, e.g., 1P:1Sn to less than 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

2.8 Method 2.6 or 2.7 comprising combining 1-10 weight % tin (II) fluoride by weight of the combination, e.g., 1-9 weight % tin (II) fluoride by weight of the combination, e.g., 2 weight % tin (II) fluoride by weight of the combination, and 1-40 weight % tetrapotassium pyrophosphate by weight of the combination, e.g., 1-30 weight % tetrapotassium pyrophosphate by weight of the combination, e.g., 1-20 weight % tetrapotassium pyrophosphate by weight of the combination, e.g., 1-10 weight % tetrapotassium pyrophosphate by weight of the combination.

2.9 Any of Method 2 or 2.1-2.5, wherein the pyrophosphate salt is tetrasodium pyrophosphate ($Na_4P_2O_7$).

2.10 Method 2.9 comprising combining the tin (II) fluoride and tetrasodium pyrophosphate in a molar ratio of 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:1Sn, e.g., 5P:1Sn.

2.11 Method 2.9 or 2.10 comprising combining 1-10 weight % tin (II) fluoride by weight of the combination, e.g., 1-9 weight % tin (II) fluoride by weight of the combination, e.g., 2 weight % tin (II) fluoride by weight of the combination, and 1-30 weight % tetrasodium pyrophosphate by weight of the combination, e.g., 1-20 weight % tetrasodium pyrophosphate by weight of the combination, e.g., 1-10 weight % tetrasodium pyrophosphate by weight of the combination.

2.12 Any of the foregoing methods comprising isolating the complex in solid form.

2.13 Any of the foregoing methods comprising lyophilizing the complex.

2.14 Any of the foregoing methods comprising isolating the complex with an anti-solvent, e.g., an organic solvent, e.g., ethanol.

2.15 An external personal care composition, e.g., an antiperspirant, deodorant, body wash, shower gel, soap (e.g., bar soap, hand soap), shampoo, hair conditioner, or cosmetic, e.g., an antiperspirant and/or deodorant, comprising an aqueous soluble tin phosphate complex made as described in any of the foregoing methods, e.g., a body wash or soap (e.g., hand soap) comprising an aqueous soluble tin phosphate complex made as described in any of the foregoing methods.

Further provided is an aqueous soluble tin phosphate complex made by any of Method 2 et seq.

Further provided is an external personal care composition (Composition 1), e.g., an antiperspirant, deodorant, body wash, shower gel, soap (e.g., bar soap, hand soap), shampoo, hair conditioner, or cosmetic, comprising tin (II) fluoride and a pyrophosphate salt, e.g., an alkali pyrophosphate salt, e.g., tetrapotassium pyrophosphate ($K_4P_2O_7$) or tetrasodium pyrophosphate ($Na_4P_2O_7$), e.g., 1.1 Composition 1 or 1.1, wherein the tin (II) fluoride and pyrophosphate salt form an aqueous soluble tin phosphate complex, e.g., any of Complex 1 et seq.

1.2 Composition 1.1, wherein the complex is formed in the composition in situ.

1.3 Composition 1.1, wherein the complex is formed in situ in an aqueous solution and combined with the composition.

1.4 Any of Composition 1.1 or 1.3, wherein the complex is combined as a solid with the composition, e.g., wherein the complex is isolated from the aqueous solution in solid form and combined with the composition.

1.5 Any of Composition 1.1, 1.3, or 1.4, wherein the complex is lyophilized and combined with the composition.

1.6 Any of Composition 1.1 or 1.3-1.5, wherein the complex is isolated with an anti-solvent, e.g., an organic solvent, e.g., ethanol, and combined with the composition.

1.7 Any of Composition 1.1-1.6, wherein the complex is made as described in any of Method 2 et seq.

1.8 Any of Composition 1.1-1.7, wherein the complex is present in an amount of 5-30 weight % by weight of the composition.

1.9 Any of the foregoing compositions, wherein the composition comprises or wherein the complex is formed from the tin (II) fluoride and pyrophosphate salt in a molar ratio of at least 1P:1Sn, e.g., 1P:1Sn to 15P:1Sn, e.g., 1P:1Sn to less than 15P:1Sn, e.g., 1P:1Sn to 10P:1Sn, e.g., 1P:1Sn to less than 10P:1Sn, e.g., P:1Sn to 5P:1Sn, e.g., 1P:1Sn to less than 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

1.10 Any of the foregoing compositions, wherein the composition comprises or wherein the complex is formed from the tin (II) fluoride and pyrophosphate salt in a molar ratio of 1P:1Sn to 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

1.11 Any of the foregoing compositions, wherein the composition comprises or wherein the complex is formed from a mixture comprising 1-10 weight % tin (II) fluoride by weight of the composition or the mixture, e.g., 1-9 weight % tin (II) fluoride by weight of the composition or the mixture, e.g., 2 weight % tin (II) fluoride by weight of the composition or the mixture, and 1-40 weight % pyrophosphate salt by weight of the composition or the mixture, e.g., 1-30 weight % pyrophosphate salt by weight of the composition or the mixture, e.g., 1-20 weight % pyrophosphate salt by weight of the composition or the mixture, e.g., 1-10 weight % pyrophosphate salt by weight of the composition or the mixture.

1.12 Any of the foregoing compositions, wherein the pyrophosphate salt is tetrapotassium pyrophosphate ($K_4P_2O_7$).

1.13 Composition 1.12, wherein the composition comprises or wherein the complex is formed from the tin (II) fluoride and tetrapotassium pyrophosphate in a molar ratio of at least 1P:1Sn, e.g., 1P:1Sn to 15P:1Sn, e.g., 1P:1Sn to less than 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, 1P:1Sn, e.g., 2P:1Sn, e.g., 5P:1Sn, e.g., 10P:1Sn, e.g., 15P:1Sn.

1.14 Composition 1.12 or 1.13, wherein the composition comprises or wherein the complex is formed from a mixture comprising 1-10 weight % tin (II) fluoride by weight of the composition or the mixture, e.g., 1-9 weight % tin (II) fluoride by weight of the composition or the mixture, e.g., 2 weight % tin (II) fluoride by weight of the composition or the mixture, and 1-40 weight % tetrapotassium pyrophosphate by weight of the composition or the mixture, e.g., 1-30 weight % tetrapotassium pyrophosphate by weight of the composition or the mixture, e.g., 1-20 weight % tetrapotassium pyrophosphate by weight of the composition or the mixture, e.g., 1-10 weight % tetrapotassium pyrophosphate by weight of the composition or the mixture.

1.15 Any of Composition 1 or 1.1-1.11, wherein the pyrophosphate salt is tetrasodium pyrophosphate ($Na_4P_2O_7$).

1.16 Composition 1.15, wherein the composition comprises or wherein the complex is formed from the tin (II) fluoride and tetrasodium pyrophosphate in a molar ratio of 1P:1Sn to 0P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:Sn, e.g., 5P:1Sn.

1.17 Composition 1.15 or 1.16, wherein the composition comprises or wherein the complex is formed from a mixture comprising 1-10 weight % tin (II) fluoride by weight of the composition or the mixture, e.g., 1-9 weight % tin (II) fluoride by weight of the composition or the mixture, e.g., 2 weight % tin (II) fluoride by weight of the composition or the mixture, and 1-30 weight % tetrasodium pyrophosphate by weight of the composition or the mixture, e.g., 1-20 weight % tetrasodium pyrophosphate by weight of the composition or the mixture, e.g., 1-10 weight % tetrasodium pyrophosphate by weight of the composition or the mixture.

1.18 Any of the foregoing compositions further comprising another antiperspirant salt comprising a polyvalent cation, e.g., antiperspirant complexes of (i) aluminum and optionally zirconium, (ii) chlorohydrate, and (iii) optionally an amino acid and/or ammonium acid, for example glycine and/or trimethylglycine, e.g., aluminum zirconium tetrachlorohydrex glycine. The complex may enhance the efficacy of the other antiperspirant salt.

1.19 Any of Composition 1 or 1.1-1.17, wherein the composition is entirely or substantially free of aluminum and optionally zirconium. For example, the compositions may include less than 2 weight % by weight of the composition, or less than 0.5 weight % by weight of the composition, or less than 0.1 weight % by weight of the composition, or less than 0.01 weight % by weight of the composition, or less than 0.001 weight % by weight of the composition, or less than 0.0001 weight % by weight of the composition, aluminum or zirconium.

1.20 Any of the foregoing compositions, wherein the composition comprises an aqueous solution.

1.21 Any of the foregoing compositions further comprising 60-85 weight % water by weight of the composition.

1.22 Any of the foregoing compositions, wherein the composition has a pH from 5-11, e.g., 5-10, e.g., 5-9, e.g., 5-8, e.g., 5-7, e.g., 5-6, e.g., 6-8 e.g., 6-7, e.g., 8-9, e.g., 9-10, e.g., 10-11.

1.23 Any of the foregoing compositions, wherein the pyrophosphate salt is tetrapotassium pyrophosphate and the composition has a pH from 5-11, e.g., 5-10, e.g., 5-9, e.g., 5-8, e.g., 5-7, e.g., 5-6, e.g., 6-8, e.g., 6-7, e.g., 9-10, e.g., 10-11.

1.24 Any of Composition 1 or 1.1-1.22, wherein the pyrophosphate salt is tetrasodium pyrophosphate and the composition has a pH from 5-9, e.g., 5-8, e.g., 5-7, e.g., 5-6, e.g., 6-8, e.g., 6-7. e.g., 8-9.

1.25 Any of the foregoing compositions, wherein the composition is an antiperspirant.

1.26 Any of the foregoing compositions, wherein the composition is a deodorant.

1.27 Any of the foregoing compositions, wherein the composition is a body wash or soap (e.g., hand soap).

1.28 Any of the foregoing compositions for use to occlude pores.

1.29 Any of the foregoing compositions for use to reduce sweat.

Further provided is a method (Method 3) to occlude pores and/or reduce sweat, in a person in need thereof comprising applying an effective amount of an external personal care composition comprising tin (II) fluoride and a pyrophosphate salt, e.g., an alkali pyrophosphate salt, e.g., tetrapotassium pyrophosphate ($K_4P_2O_7$) (TKPP) or tetrasodium pyrophosphate ($Na_4P_2O_7$) (TSPP), e.g., any of Composition 1 et seq., to the skin of the person, e.g., 3.1 Method 3, wherein the tin (II) fluoride and pyrophosphate salt, e.g., alkali pyrophosphate salt, form an aqueous soluble tin phosphate complex, e.g., any of Complex 1 et seq.

3.2 Method 3.1, wherein the complex is formed in situ in the composition, e.g., wherein the composition has a pH from 5-1, e.g., 5-10, e.g., 5-9, e.g., 5-8, e.g., 5-7, e.g., 5-6, e.g., 6-8, e.g., 6-7, e.g., 8-9, e.g., 9-10, e.g., 10-11. Method 3.1, wherein the pyrophosphate salt is tetrapotassium pyrophosphate and the composition has a pH from 5-11, e.g., 5-10, e.g., 5-9, e.g., 5-8, e.g., 5-7, e.g., 5-6, e.g., 6-8, e.g., 6-7, e.g., 9-10, e.g., 10-11. Method 3.1, wherein the pyrophosphate salt is tetrasodium pyrophosphate and the composition has a pH from 5-9, e.g., 5-8, e.g., 5-7, e.g., 5-6, e.g., 6-8, e.g., 6-7, e.g., 8-9.

3.3 Method 3.1, wherein the complex is formed in situ in an aqueous solution and combined with the composition, e.g., wherein the aqueous solution has a pH from 5-11, e.g., 5-10, e.g., 5-9, e.g., 5-8, e.g., 5-7, e.g., 5-6, e.g., 6-8, e.g., 6-7, e.g., 8-9, e.g., 9-10, e.g., 10-11. Method 3.1, wherein the pyrophosphate salt is tetrapotassium pyrophosphate and the aqueous solution has a pH from 5-11, e.g., 5-10, e.g., 5-9, e.g., 5-8, e.g., 5-7, e.g., 5-6, e.g., 6-8, e.g., 6-7, e.g., 9-10, e.g., 10-11. Method 3.1, wherein the pyrophosphate salt is tetrasodium pyrophosphate and the aqueous solution has a pH from 5-9, e.g., 5-8, e.g., 5-7, e.g., 5-6, e.g., 6-8, e.g., 6-7, e.g., 8-9.

3.4 Method 3.1 or 3.3, wherein the complex is combined as a solid with the composition, e.g., wherein the complex is isolated from the aqueous solution in solid form and combined with the composition.

3.5 Any of Method 3.1, 3.3, or 3.4, wherein the complex is lyophilized and combined with the composition.

3.6 Any of Method 3.1 or 3.3-3.5, wherein the complex is isolated with an anti-solvent, e.g., an organic solvent, e.g., ethanol, and combined with the composition.

3.7 Any of Method 3.1-3.6, wherein the complex is made as described in any of Method 2 et seq.

3.8 Any of Method 3.1-3.7, wherein the complex is present in an amount of 5-30 weight % by weight of the composition.

3.9 Any of the foregoing methods, wherein the composition comprises or wherein the complex is formed from the tin (II) fluoride and pyrophosphate salt in a molar ratio of at least 1P:1Sn, e.g., 1P:1Sn to 15P:1Sn, e.g., 1P:1Sn to less than 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

3.10 Any of the foregoing methods, wherein the composition comprises or wherein the complex is formed from the tin (II) fluoride and pyrophosphate salt in a molar ratio of 1P:1Sn to 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

3.11 Any of the foregoing methods, wherein the composition comprises or wherein the complex is formed from a mixture comprising 1-10 weight % tin (II) fluoride by weight of the composition or the mixture, e.g., 1-9 weight % tin (II) fluoride by weight of the composition or the mixture, e.g., 2 weight % tin (II) fluoride by weight of the composition or the mixture, and 1-10 weight % pyrophosphate salt by weight of the composition or the mixture, e.g., 3-4 weight % pyrophosphate salt by weight of the composition or the mixture, e.g., 7-8 weight % pyrophosphate salt by weight of the composition or the mixture.

3.12 Any of the foregoing methods, wherein the pyrophosphate salt is tetrapotassium pyrophosphate.

3.13 Method 3.12, wherein the composition comprises or wherein the complex is formed from the tin (II) fluoride and tetrapotassium pyrophosphate in a molar ratio of at least 1P:1Sn, e.g., 1P:1Sn to 15P:1Sn, e.g., 1P:1Sn to less than 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1 Sn.

3.14 Method 3.12 or 3.13, wherein the composition comprises or wherein the complex is formed from a mixture comprising 1-10 weight % tin (II) fluoride by weight of the composition or the mixture, e.g., 1-9 weight % tin (II) fluoride by weight of the composition or the mixture, e.g., 2 weight % tin (II) fluoride by weight of the composition or the mixture, and 1-40 weight % tetrapotassium pyrophosphate by weight of the composition or the mixture, e.g., 1-30 weight % tetrapotassium pyrophosphate by weight of the composition or the mixture, e.g., 1-20 weight % tetrapotassium pyrophosphate by weight of the composition or the mixture, e.g., 1-10 weight % tetrapotassium pyrophosphate by weight of the composition or the mixture.

3.15 Any of Method 3 or 3.1-3.11, wherein the pyrophosphate salt is tetrasodium pyrophosphate.

3.16 Method 3.15, wherein the composition comprises or wherein the complex is formed from the tin (II) fluoride and tetrasodium pyrophosphate in a molar ratio of 1P:1 Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:1Sn, e.g., 5P:1Sn.

3.17 Method 3.15 or 3.16, wherein the composition comprises or wherein the complex is formed from a mixture comprising 1-10 weight % tin (II) fluoride by weight of the composition or the mixture, e.g., 1-9 weight % tin (II) fluoride by weight of the composition or the mixture, e.g., 2 weight % tin (II) fluoride by weight of the composition or the mixture, and 1-30 weight % tetrasodium pyrophosphate by weight of the composition or the mixture, e.g., 1-20 weight % tetrasodium pyrophosphate by weight of the composition or the mixture, e.g., 1-10 weight % tetrasodium pyrophosphate by weight of the composition or the mixture.

3.18 Any of the foregoing methods, wherein the composition further comprises another antiperspirant salt comprising a polyvalent cation, e.g., antiperspirant complexes of (i) aluminum and optionally zirconium, (ii) chlorohydrate, and (iii) optionally an amino acid and/or ammonium acid, for example glycine and/or trimethylglycine, e.g., aluminum zirconium tetrachlorohydrex glycine. The complex may enhance the efficacy of the other antiperspirant salt.

3.19 Any of Method 3 or 3.1-3.17, wherein the composition is entirely or substantially free of aluminum and optionally zirconium. For example, the compositions may include less than 2 weight % by weight of the composition, or less than 0.5 weight % by weight of the composition, or less than 0.1 weight % by weight of the composition, or less than 0.01 weight % by weight of the composition, or less than 0.001 weight % by weight of the composition, or less than 0.0001 weight % by weight of the composition, aluminum or zirconium.

3.20 Any of the foregoing methods, wherein the composition comprises an aqueous solution.

3.21 Any of the foregoing methods, wherein the composition further comprises 60-85 weight % water by weight of the composition.

3.22 Any of the foregoing methods, wherein the pH of the composition is from 5-11, e.g., 5-10, e.g., 5-9, e.g., 5-6, e.g., 6-7, e.g., 8-9, e.g., 9-10, e.g., 10-11.

3.23 Any of the foregoing methods, wherein the pyrophosphate salt is tetrapotassium pyrophosphate and the composition has a pH from 5-11, e.g., 5-10, e.g., 5-9, e.g., 5-6, e.g., 6-7, e.g., 9-10, e.g., 10-11.

3.24 Any of Method 3 or 3.1-3.22, wherein the pyrophosphate salt is tetrasodium pyrophosphate and the composition has a pH from 5-9, e.g., 5-6, e.g., 6-7, e.g., 8-9.

3.25 Any of the foregoing methods, wherein the method is to occlude pores.

3.26 Any of the foregoing methods, wherein the method is to reduce sweat.

3.27 Any of the foregoing methods, wherein the composition is any of Composition 1 et seq.

3.28 Any of the foregoing methods, wherein the composition is an antiperspirant.

3.29 Any of the foregoing methods, wherein the composition is a deodorant.

Further provided is a method (Method 4) of making an external personal care composition comprising tin (II) fluoride and a pyrophosphate salt, e.g., tetrapotassium pyrophosphate ($K_4P_2O_7$) (TKPP) or tetrasodium pyrophosphate ($Na_4P_2O_7$) (TSPP), e.g., any of Composition 1 et seq., comprising mixing the tin (II) fluoride and a pyrophosphate salt, e.g., an alkali pyrophosphate salt, with a personal care carrier, e.g., 4.1 Method 4, wherein the tin (II) fluoride and pyrophosphate salt, e.g., alkali pyrophosphate salt, e.g., tetrapotassium pyrophosphate or tetrasodium pyrophosphate, form an aqueous soluble tin phosphate complex, e.g., any of Complex 1 et seq.

4.2 Method 4.1, wherein the complex is formed in situ in the composition, e.g., wherein the composition has a pH from 5-11, e.g., 5-10, e.g., 5-9, e.g., 5-8, e.g., 5-7, e.g., 5-6, e.g., 6-8, e.g., 6-7, e.g., 8-9, e.g., 9-10, e.g., 10-11. Method 4.1, wherein the pyrophosphate salt is tetrapotassium pyrophosphate and the composition has a pH from 5-11, e.g., 5-10, e.g., 5-9, e.g., 5-8, e.g., 5-7, e.g., 5-6, e.g., 6-8, e.g., 6-7, e.g., 9-10, e.g., 10-11. Method 4.1, wherein the pyrophosphate salt is tetrasodium pyrophosphate and the composition has a pH from 5-9, e.g., 5-8, e.g., 5-7, e.g., 5-6, e.g., 6-8, e.g., 6-7, e.g., 8-9.

4.3 Method 4.1, wherein the complex is formed in situ in an aqueous solution and combined with the personal care carrier, e.g., wherein the aqueous solution has a pH from 5-11, e.g., 5-10, e.g., 5-9, e.g., 5-8, e.g., 5-7, e.g., 5-6, e.g., 6-8, e.g., 6-7, e.g., 8-9, e.g., 9-10, e.g., 10-11. Method 4.1, wherein the pyrophosphate salt is tetrapotassium pyrophosphate and the aqueous solution has a pH from 5-11, e.g., 5-10, e.g., 5-9, e.g., 5-8, e.g., 5-7, e.g., 5-6, e.g., 6-8, e.g., 6-7, e.g., 9-10, e.g., 10-11. Method 4.1, wherein the pyrophosphate salt is tetrasodium pyrophosphate and the aqueous solution has a pH from 5-9, e.g., 5-8, e.g., 5-7, e.g., 5-6, e.g., 6-8, e.g., 6-7, e.g., 8-9.

4.4 Method 4.1 or 4.3, wherein the complex is combined as a solid with the personal care carrier, e.g., wherein the complex is isolated from the aqueous solution in solid form and combined with the personal care carrier, e.g., an antiperspirant and/or deodorant carrier, e.g., an antiperspirant carrier, e.g., a deodorant carrier.

4.5 Any of Method 4.1, 4.3, or 4.4, wherein the complex is lyophilized and combined with the personal care carrier, e.g., an antiperspirant and/or deodorant carrier, e.g., an antiperspirant carrier, e.g., a deodorant carrier.

4.6 Any of Method 4.1 or 4.3-4.5, wherein the complex is isolated with an anti-solvent, e.g., an organic solvent, e.g., ethanol, and combined with the personal care carrier, e.g., an antiperspirant and/or deodorant carrier, e.g., an antiperspirant carrier, e.g., a deodorant carrier.

4.7 Any of Method 4.1-4.6, wherein the complex is made as described in any of Method 2 et seq.

4.8 Any of Method 4.1-4.7, wherein the complex is present in an amount of 5-30 weight % by weight of the composition.

4.9 Any of the foregoing methods comprising mixing the tin (II) fluoride and pyrophosphate salt, e.g., alkali pyrophosphate salt, in a molar ratio of at least 1P:1Sn, e.g., 1P:1Sn to 15P:1Sn, e.g., 1P:1Sn to less than 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

4.10 Any of the foregoing methods comprising mixing the tin (II) fluoride and pyrophosphate salt, e.g., alkali pyrophosphate salt, in a molar ratio of 1P:1Sn to 15P:1Sn, e.g., 1P:1Sn to 10P:1Sn, e.g., 1P:1Sn to less than 0P:1Sn, e.g., 1P:1Sn to 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

4.11 Any of the foregoing methods comprising mixing 1-10 weight % tin (II) fluoride by weight of the mixture, e.g., 1-9 weight % tin (II) fluoride by weight of the mixture, e.g., 2 weight % tin (II) fluoride by weight of the mixture, and 1-10 weight % pyrophosphate salt, e.g., alkali pyrophosphate salt, by weight of the mixture, e.g., 3-4 weight % pyrophosphate salt, e.g., alkali pyrophosphate salt, by weight of the mixture, e.g., 7-8 weight % pyrophosphate salt, e.g., alkali pyrophosphate salt, by weight of the mixture.

4.12 Any of the foregoing methods, wherein the pyrophosphate salt is tetrapotassium pyrophosphate.

4.13 Method 4.12 comprising mixing the tin (II) fluoride and tetrapotassium pyrophosphate salt in a molar ratio of at least 1P:1Sn, e.g., P:1Sn to 15P:1Sn, e.g., 1P:1Sn to less than 15P:1Sn, e.g., 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:1Sn, e.g., 5P:1Sn, e.g., 10P:1Sn, e.g., 15P:1Sn.

4.14 Method 4.12 or 4.13 comprising mixing 1-10 weight % tin (II) fluoride by weight of the mixture, e.g., 1-9 weight % tin (II) fluoride by weight of the mixture, e.g., 2 weight % tin (II) fluoride by weight of the mixture, and 1-40 weight % tetrapotassium pyrophosphate by weight of the mixture, e.g., 1-30 weight % tetrapotassium pyrophosphate by weight of the mixture, e.g., 1-20 weight % tetrapotassium pyrophosphate by weight of the mixture, e.g., 1-10 weight % tetrapotassium pyrophosphate by weight of the mixture.

4.15 Any of Method 4 or 4.1-4.11, wherein the pyrophosphate salt is tetrasodium pyrophosphate.

4.16 Method 4.15 comprising mixing the tin (II) fluoride and tetrasodium pyrophosphate salt in a molar ratio of 1P:1Sn to 10P:1Sn, e.g., 1P:1Sn to less than 10P:1Sn, e.g., 1P:1Sn to 5P:1Sn, e.g., 1P:1Sn to less than 5P:1Sn, e.g., 1P:1Sn to 2P:1Sn, e.g., 1P:1Sn, e.g., 2P:1Sn. e.g., 5P:1Sn.

4.17 Method 4.15 or 4.16 comprising mixing 1-10 weight % tin (II) fluoride by weight of the mixture, e.g., 1-9 weight % tin (II) fluoride by weight of the mixture, e.g., 2 weight % tin (II) fluoride by weight of the mixture, and 1-30 weight % tetrasodium pyrophosphate by weight of the mixture, e.g., 1-20 weight % tetrasodium pyrophosphate by weight of the mixture, e.g., 1-10 weight % tetrasodium pyrophosphate by weight of the mixture.

4.18 Any of the foregoing methods, wherein the personal care carrier is an antiperspirant carrier.

4.19 Any of the foregoing methods, wherein the personal care carrier is a deodorant carrier.

Tin (II) fluoride and a pyrophosphate salt, e.g., an alkali pyrophosphate salt, e.g., tetrapotassium pyrophosphate ($K_4P_2O_7$) (TKPP) or tetrasodium pyrophosphate ($Na_4P_2O_7$) (TSPP), may be combined to form a pre-formed aqueous soluble tin phosphate complex, e.g., any of Complex 1 et seq., which may be prepared in bulk, and then incorporated into the external personal care compositions disclosed herein, e.g., any of Composition 1 et seq. Alternatively, tin (II) fluoride and a pyrophosphate salt, e.g., tetrapotassium pyrophosphate ($K_4P_2O_7$) (TKPP) or tetrasodium pyrophosphate ($Na_4P_2O_7$) (TSPP), may be combined during the manufacture of the external personal care compositions disclosed herein, e.g., any of Composition 1 et seq., to form the complex in situ in the composition.

For antiperspirant and/or deodorants, the carrier can be any carrier that is used for antiperspirants and/or deodorants. The carrier can be in the form of a stick, a gel, a roll-on, or an aerosol (e.g. spray). For stick compositions, the carrier may include oils and/or silicones and gelling agents.

Optional ingredients that may be included in an antiperspirant and/or deodorant disclosed herein, e.g., any of Composition 1 et seq., include solvents; water-soluble alcohols such as $C_{2-8}$ alcohols; glycols; glycerides including mono-, di- and triglycerides; medium to long chain organic acids, alcohols, and esters; surfactants including emulsifying and dispersing agents; amino acids; structurants including thickeners and gelling agents, for example polymers, silicates, and silicon dioxide; emollients; fragrances; and colorants including dyes and pigments.

The complexes disclosed herein, e.g., any of Complex 1 et seq., can be formulated into topical antiperspirants and/or deodorants suitable for application to skin, illustratively a stick, a gel, a cream, a roll-on, a soft solid, a powder, a liquid, an emulsion, a suspension, a dispersion, or a spray. The compositions disclosed herein, e.g., any of Composition 1 et seq., can comprise a single phase or can be a multi-phase system, for example a system comprising a polar phase and an oil phase, optionally in the form of a stable emulsion. The compositions disclosed herein, e.g., any of Composition 1 et seq., can be liquid, semi-solid, or solid. Antiperspirants and/or deodorants may be provided in any suitable container such as an aerosol can, tube, or container with a porous cap, roll-on container, bottle, container with an open end, etc.

The complexes disclosed herein, e.g., any of Complex 1 et seq., can be formulated into body washes and soaps (e.g., hand soaps).

The complexes and compositions disclosed herein, e.g., any of Complex 1 et seq., e.g., any of Composition 1 et seq., may be destructive to or inhibit the growth of bacteria. For instance, the complexes disclosed herein, e.g., any of Complex 1 et seq., may act as a preservative system. In addition, the formation of precipitate of the complexes and compositions disclosed herein, e.g., any of Complex 1 et seq., e.g., any of Composition 1 et seq., may provide a residual antibacterial effect.

The complexes and compositions disclosed herein, e.g., any of Complex 1 et seq., e.g., any of Composition 1 et seq., may be used in a method to reduce sweating by applying the complex and/or composition to skin. In certain embodiments, the application is to axilla. Thus, provided is a method for controlling perspiration comprising applying to skin an antiperspirant effective amount of a complex or a composition disclosed herein, e.g., any of Complex 1 et seq., e.g., any of Composition 1 et seq.

A complex disclosed herein may be described by reference to a spectrum as "substantially" shown or depicted in a figure or by one or more data points. It will be appreciated that a Fourier transform infrared, Raman, or NMR spectrum of a given sample may vary depending on factors known to those of skill in the art, e.g., instrument used, etc. Therefore, the Fourier transform infrared, Raman, and NMR spectrum peaks set forth herein will have an acceptable level of deviation. For example, for Fourier transform infrared spectra, the peaks may have an acceptable deviation of e.g., ±20 $cm^{-1}$ or ±16 $cm^{-1}$ or ±4 $cm^{-1}$ or ±2 $cm^{-1}$ or ±1 $cm^{-1}$ or ±0.5 $cm^{-1}$. For example, for Raman spectra, the peaks may have an acceptable deviation of, e.g., ±1-2 $cm^{-1}$, e.g., ±1 $cm^{-1}$, e.g., ±2 $cm^{-1}$. For example, for NMR spectra, the peaks may have an acceptable deviation of, e.g., ±1 ppm.

As used herein, "external" means suitable for application to the skin, including the scalp, and nails.

As used herein, "aqueous solution" means a solution in which the solvent is water.

As used herein, "aqueous soluble tin phosphate complex" includes a complex in which 1 gram of the complex is soluble in 1 or 10 to 100 ml water, e.g., 1 or 10 to 90 ml water, e.g., 1 or 10 to 80 ml water, e.g., 1 or 10 to 70 ml water, e.g., 1 or 10 to 60 ml water, e.g., 1 or 10 to 50 ml water, e.g., 1 or 10 to 40 ml water, e.g., 1 or 10 to 30 ml water, e.g., 1 or 10 to 20 ml water, e.g., 1-10 ml water, e.g., less than 1 ml water.

EXAMPLES

Example 1

TABLE 1

Stannous Fluoride Stock Solution Preparation

| % $SnF_2$ | $SnF_2$ (g) | Total (g) |
|---|---|---|
| 20 | 4 | 20 |

TABLE 2

Tetrasodium Pyrophosphate (TSPP) Solution Preparation

| P:Sn Molar Ratio | TSPP (g) | $SnF_2$ Sol (g) | Total (g) | pH |
|---|---|---|---|---|
| 0.5 | 0.08 | 1 | 10 | |
| 1 | 0.2 | 1 | 10 | 5.5 |
| 2 | 0.3 | 1 | 10 | 6.6 |
| 5 | 0.8 | 1 | 10 | 8.8 |
| 10 | 1.7 | 1 | 10 | |

TABLE 3

Tetrapotassium Pyrophosphate (TKPP) Solution Preparation

| P:Sn Molar Ratio | TKPP (g) | $SnF_2$ Sol (g) | Total (g) | pH |
|---|---|---|---|---|
| 0.5 | 0.1 | 1 | 10 | |
| 1 | 0.2 | 1 | 10 | 5.6 |
| 2 | 0.4 | 1 | 10 | 6.8 |

TABLE 3-continued

Tetrapotassium Pyrophosphate (TKPP) Solution Preparation

| P:Sn Molar Ratio | TKPP (g) | $SnF_2$ Sol (g) | Total (g) | pH |
|---|---|---|---|---|
| 5 | 1.1 | 1 | 10 | 9.3 |
| 10 | 2.1 | 1 | 10 | 10.0 |
| 15 | 3.2 | 1 | 10 | 10.4 |

The solutions are prepared by first dissolving TSPP or TKPP in water (mixing under high heat if necessary) and then adding a 20% stannous fluoride solution to the clear solution with an automatic pipet. The pH of all clear solutions is recorded. All of the solutions contain 2% $SnF_2$.

With TSPP, clear solutions are observed for solutions with P/Sn molar ratios of 1, 2, and 5. At molar ratios 10 and greater, TSPP does not fully dissolve.

With TKPP, clear solutions are observed for all tested P/Sn molar ratios greater than or equal to 1. TKPP is more water soluble than TSPP.

Solutions are aged overnight at room temperature. A 2% stannous fluoride solution is used as a control, which shows precipitate almost immediately after dissolution. After overnight aging, TSPP solutions with a P/Sn molar ratio spanning from 1 to 5 remain clear. After overnight aging, TKPP solutions with a P/Sn molar ratio spanning from 1 to 15 remain clear.

All stable solutions remain stable after 4 weeks of aging at room temperature.

Example 2

TABLE 4

Preparation of 1% Bovine Serum Albumin (BSA) Solutions

| Sample | Amount of BSA (g) | Amount of Total Solution (g) |
|---|---|---|
| TSPP 1Sn:1P solution | 0.03 | 3 |
| TSPP 1Sn:2P solution | 0.03 | 3 |
| TSPP 1Sn:5P solution | 0.03 | 3 |
| TKPP 1Sn:1P solution | 0.03 | 3 |
| TKPP 1Sn:2P solution | 0.03 | 3 |
| TKPP 1Sn:5P solution | 0.03 | 3 |
| TKPP 1Sn:10P solution | 0.03 | 3 |
| TKPP 1Sn:15P solution | 0.03 | 3 |
| Control:1% BSA in DI water | 0.03 | 3 |

Bovine serum albumin (BSA) simulates sweat proteins and may reveal the benefit of the complex in antiperspirants, as the formation of precipitate may block sweat ducts.

Aging of the BSA Solutions

Bovine serum albumin (BSA) is used to model interaction of solutions with skin protein. Clear TSPP and TKPP solutions are aged at 37° C. overnight after the addition of 1% BSA.

All three solutions of $SnF_2$+TSPP (P/Sn molar ratios of 1, 2, and 5) with 1% BSA form a precipitate after aging overnight at 37° C.

Solutions of $SnF_2$+TKPP with P/Sn molar ratios of 1, 2, 5, and 10 with 1% BSA form a precipitate after aging overnight at 37° C. The solution with a P/Sn molar ratio of 15 fails to completely dissolve the BSA, and no change is observed overnight.

A 1% BSA control after aging overnight at room temperature shows no precipitate. A 1% BSA control after aging overnight at 37° C. shows no precipitate.

Example 3

A clear solution comprising 2% stannous fluoride ($SnF_2$) and tetrasodium pyrophosphate (TSPP) with a P:Sn molar ratio of 1 is lyophilized using a Labconco FreeZone 2.5 Freeze Dryer. FTIR-ATR analysis is conducted on freeze dried powder on an extended range Spectrum One Perkin Elmer system featuring a CsI beam splitter, DTGS detector, and single-bounce diamond KRS-5 ATR crystal. Sample is placed directly on the ATR diamond. See FIG. 1. Peaks observed for the Sn-TSPP complex are listed in Table 5 (broad peaks from water/ethanol at about 1640 and 3200 $cm^{-1}$ are omitted from peak table).

TABLE 5

| Wavenumber ($cm^{-1}$) | Absorbance (A) |
| --- | --- |
| 481 | 0.6901 |
| 546 | 0.9997 |
| 722 | 0.3353 |
| 881 | 0.7443 |
| 979 | 0.4082 |
| 1081 | 0.5859 |
| 1101 | 0.5938 |

Figure 5:
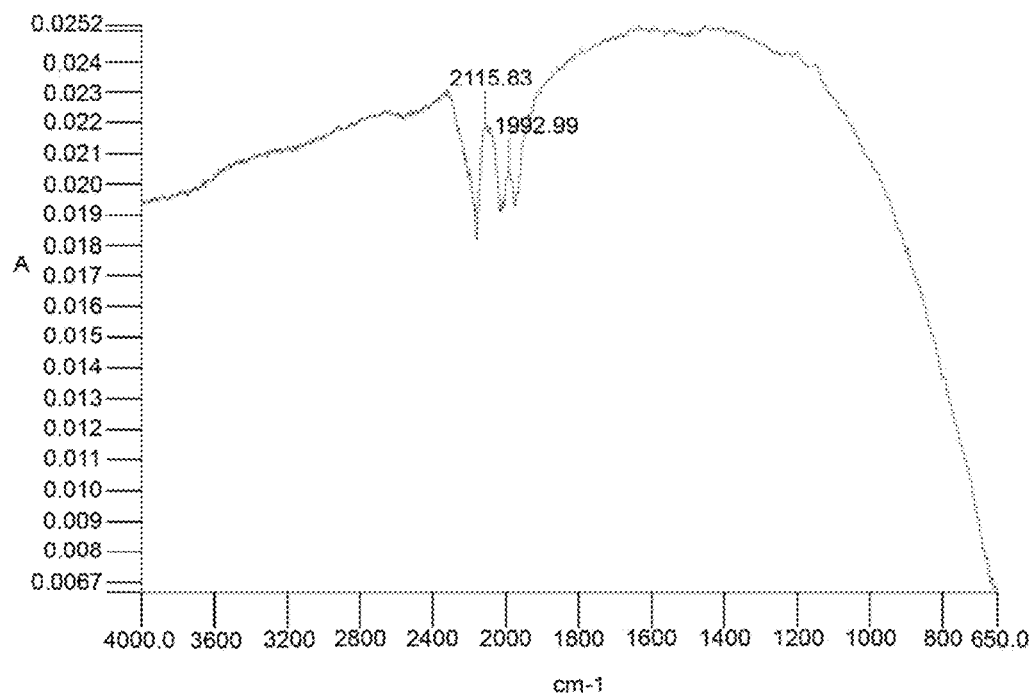
FIG. 5 is a Fourier transform infrared spectrum of $SnF_2$.

Ethanol is added dropwise to a clear solution comprising 2% stannous fluoride ($SnF_2$) and tetrasodium pyrophosphate (TSPP) with a P:Sn molar ratio of 1 until precipitate forms. Solid is filtered and air dried. FTIR-ATR analysis is conducted on solid on an extended range Spectrum One Perkin Elmer system featuring a CsI beam splitter, DTGS detector, and single-bounce diamond KRS-5 ATR crystal. Sample is placed directly on the ATR diamond. See FIG. 2. An FTIR-ATR for solid $SnF_2$ is in FIG. 5.

FTIR-ATR analysis may be conducted on about 10-100 mg of solid.

Example 4

Solutions of 2% $SnF_2$ and TSPP in water with P/Sn molar ratios of 1, 2, and 5 are prepared. The solutions are analyzed as-prepared on an Agiltron PeakSeeker Raman System equipped with a fiber optic probe designed for liquid samples. The spectra, obtained in 30 second integration times, is compared to that of scintillation vials containing deionized water as a blank using RSIQ software. Raman spectra for the solutions are shown in FIG. 6 and peaks are listed in Table 6 (below).

TABLE 6

| Sample | Raman Shift ($cm^{-1}$) |
| --- | --- |
| P/Sn 1 | None |
| P/Sn 2 | 1022 |
| P/Sn 5 | 1022 |

Example 5

A 2% $SnF_2$ solution with TSPP at a P:Sn molar ratio of 1 is prepared in a 50 mL centrifuge vial according to the following: 0.8 g $SnF_2$, 0.5 g TSPP, 40 g total (with $H_2O$). Vortex and sonicate until solution is clear. Roughly 32.5 mL is left in the centrifuge vial while the rest is transferred to a scintillation vial. To the 32.5 mL, 18 g 100% EtOH is added, yielding an opaque solution that settles a white precipitate to the bottom. The solution becomes opaque once >13.58 g EtOH is added. The sample is left overnight at room temperature. The solid is centrifuged, decanted, and washed with EtOH.

Elemental analysis of the solid is obtained providing a P:Sn:Na molar ratio. Fluoride is calculated based on charge neutrality (assuming Sn remains in +2 oxidation state). Prior to analysis, the solid is dissolved in nitric acid. Phosphorous is quantified via ICP-OES, while Na and Sn are quantified using AAS.

TABLE 7

| Results: 1 pyrophosphate$^{4-}$ ($P_2O_7^{4-}$):1 $Na^+$:2 $Su^{2+}$:1 $F^-$ | | | |
| --- | --- | --- | --- |
| | % | mmol | Mol Ratio |
| Phosphorus | 12.30 | 3.97 | 2 |
| Sodium | 4.64 | 2.02 | 1 |
| Tin | 47.54 | 4.00 | 2 |

Example 6

Figure 7:
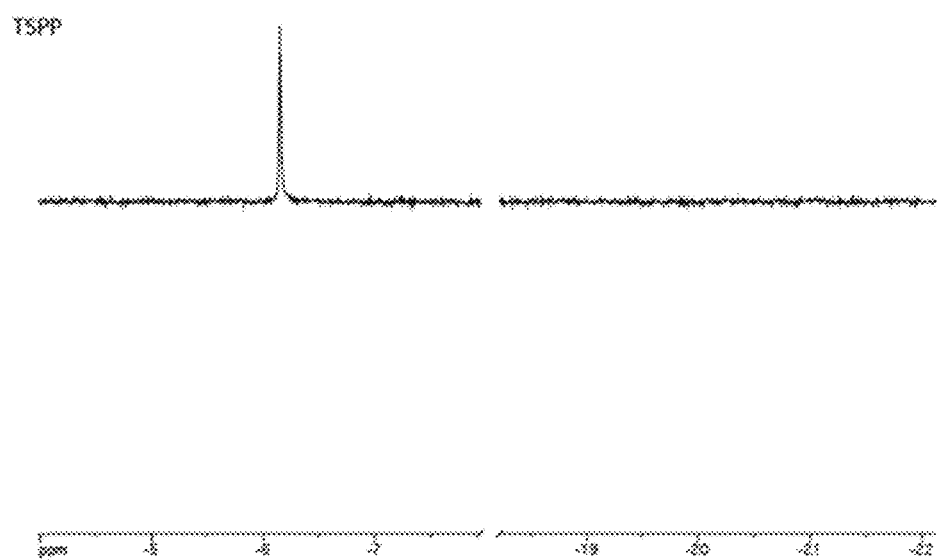
FIG. 7 depicts a $^{31}$P NMR spectrum of a solution of TSPP.

Solutions of 2% $SnF_2$ and TSPP in water with P/Sn molar ratios of 1, 2, and 5 are prepared. 5 weight % $D_2O$ is added to the solutions. $^{31}P$ and $^{119}Sn$ NMR are acquired on a Bruker AVANCE 500 spectrometer working at 202.4 MHz for $^{31}P$ NMR and 163.5 MHz for $^{119}Sn$ NMR at room temperature. $^{31}P$ NMR are externally referenced to 85% $H_3PO_4$ set to 0 ppm. $^{119}Sn$ NMR are externally referenced to saturated $SnF_2$ in $D_2O$ at −796 ppm prepared right before measurement. FIGS. 3a, 3b, and 3c depict $^{31}P$ NMR spectra of solutions with P:Sn molar ratios of 5 (FIG. 3a), 2 (FIG. 3b), and 1 (FIG. 3c). FIGS. 4a, 4b, and 4c depict $^{119}Sn$ NMR spectra of solutions with P:Sn molar ratios of 5 (FIG. 4a), 2 (FIG. 4b), and 1 (FIG. 4c). $^{31}P$ NMR peaks are listed in Table 8 and $^{119}Sn$ NMR peaks are listed in Table 9. A $^{31}P$ NMR spectrum of a solution of TSPP in water with 5 weight % $D_2O$ added and externally referenced to 85% $H_3PO_4$ set to 0 ppm is in FIG. 7.

TABLE 8

| | P/Sn Molar Ratio | $^{31}P$ Chemical Shift (ppm) |
| --- | --- | --- |
| $SnF_2$-TSPP | 5 | −6.30 |
| | | −9.82 |
| | | −10.23 (doublet) |
| | | −10.31 (doublet) |
| $SnF_2$-TSPP | 2 | −8.34 |
| | | −9.78 |
| | | −10.49 |
| | | −10.69 |
| | | −11.09 |
| $SnF_2$-TSPP | 1 | 2.10 |
| | | 2.22 |
| | | −9.03 |
| | | −9.31 |
| | | −9.65 |
| | | −9.74 |
| | | −10.36 |
| | | −11.22 |
| | | −11.40 |
| | | −12.77 |
| | | −14.35 |

TABLE 9

| | P/Sn Molar Ratio | $^{119}Sn$ Chemical Shift (ppm) |
| --- | --- | --- |
| $SnF_2$-TSPP | 5 | −640.43 |
| | | −686.58 |
| | | −693.76 |

TABLE 9-continued

| | P/Sn Molar Ratio | $^{119}$Sn Chemical Shift (ppm) |
|---|---|---|
| SnF$_2$-TSPP | 2 | −642.35 |
| | | −678.79 |
| | | −724.61 |
| SnF$_2$-TSPP | 1 | −672.97 |
| | | −686.36 |
| | | −696.08 |
| | | −705.84 |
| | | −734.85 |
| | | −742.85 |
| | | −747.93 |
| | | −754.99 |
| | | −764.39 |
| | | −766.74 |
| | | −773.79 |
| | | −804.84 |
| | | −813.14 |
| | | −821.45 |

Example 7

A roll-on antiperspirant comprising the aqueous soluble tin phosphate complex as disclosed herein can be formulated as described in Table 10 (below).

TABLE 10

| Material | Weight Percent |
|---|---|
| Aqueous soluble tin phosphate complex | 5-30% |
| Surfactant(s) | 1-30%, e.g., 5% |
| Emollient(s) | 1-10%, e.g, 2% |
| Silicone(s) | 1-10%, e.g., 2% |
| Fragrance(s) | 0.5-5%, e.g., 1% |
| Water | Q.S. |

Example 8

TABLE 11

Tetrasodium Pyrophosphate (TSPP) Solution Preparation
Solution Preparation (TSPP in 3% SnCl$_2$•2H$_2$O)

| P:Sn Molar Ratio | TSPP (g) | SnCl$_2$•2H$_2$O (g) | Total (g) |
|---|---|---|---|
| 0.5 | 0.2 | 0.6 | 20 |
| 1 | 0.3 | 0.6 | 20 |
| 2 | 0.7 | 0.6 | 20 |
| 5 | 1.7 | 0.6 | 20 |
| 10 | TSPP not soluble | | |

Solutions are prepared by dissolving TSPP in deionized water (mixing under heat if necessary) and then adding 0.6 g of SnCl$_2$.2H$_2$O to make 20-gram solutions.

The solutions with a P/Sn molar ratio spanning from 0.5 to 5 containing 3% SnCl$_2$.2H$_2$O are aged overnight at room temperature. A 3% SnCl$_2$.2H$_2$O solution is used as a control. The control, 0.5:1, and 1:1 solutions each form a cloudy precipitate that settles after aging overnight. The 2:1 and 5:1 solutions form crystals immediately after the addition of SnCl$_2$.2H$_2$O. The crystals dissolve after aging for one week.

Example 9

TABLE 12

Tetraspotassium Pyrophosphate (TKPP) Solution Preparation
Solution Preparation (TKPP in 3% SnCl$_2$•2H$_2$O)

| P:Sn Molar Ratio | TKPP (g) | SnCl$_2$•2H$_2$O (g) | Total (g) |
|---|---|---|---|
| 0.5 | 0.2 | 0.6 | 20 |
| 1 | 0.4 | 0.6 | 20 |
| 2 | 0.8 | 0.6 | 20 |
| 5 | 2.1 | 0.6 | 20 |
| 10 | 4.2 | 0.6 | 20 |
| 15 | 6.3 | 0.6 | 20 |

Solutions are prepared by dissolving TKPP in deionized water (mixing under heat if necessary) and then adding 0.6 g SnCl$_2$.2H$_2$O to make 20-g solutions.

The solutions with a P/Sn molar ratio spanning from 0.5 to 5 containing 3% SnCl$_2$.2H$_2$O are aged overnight at room temperature. A 3% SnCl$_2$.2H$_2$O solution is used as a control. The control, 0.5:1, and 1:1 solutions each form a cloudy precipitate that settles after aging overnight. The 2:1 solution forms a precipitate that settles immediately. The 5:1, 10:1, and 15:1 solutions are mostly clear with a small amount (decreasing as phosphate amount increases) of precipitate at the bottom of each vial. The amount of precipitate decreases after aging, but the precipitate never fully dissolves.

What is claimed is:

1. An external personal care composition comprising tin (II) fluoride and a pyrophosphate salt, wherein the tin (II) fluoride and pyrophosphate salt form an aqueous soluble tin phosphate complex, wherein the composition is an antiperspirant or a deodorant further comprising a surfactant, an emollient, a silicone, and water;
    wherein the complex is present in an amount of 5 to 30 weight % by weight of the composition,
    wherein the emollient is present in an amount of 1 to 10 weight % by weight of the composition,
    wherein the silicone is present in an amount of 1 to 10 weight % by weight of the composition, and
    wherein water is present in an amount of 60 to 85 weight % by weight of the composition.

2. The composition of claim 1, wherein the complex is formed in the composition in situ.

3. The composition of claim 1, wherein the complex is formed in situ in an aqueous solution and combined with the composition.

4. The composition of claim 3, wherein the complex is isolated from the aqueous solution in solid form and combined with the composition.

5. The composition of claim 1, wherein the complex is lyophilized and combined with the composition.

6. The composition of claim 1, wherein the complex is isolated with an anti-solvent and combined with the composition.

7. The composition of claim 1, wherein the composition comprises the tin (II) fluoride and pyrophosphate salt in a molar ratio of at least 1P:1Sn, wherein P is phosphorous.

8. The composition of claim 1, wherein the composition comprises the tin (II) fluoride and pyrophosphate salt in a molar ratio of 1P:1Sn to 15P:1Sn, wherein P is phosphorous.

9. The composition of claim 1, wherein the composition comprises 1 to 10 weight % tin (II) fluoride by weight of the composition and 1 to 40 weight % pyrophosphate salt by weight of the composition.

10. The composition of claim 1, wherein the pyrophosphate salt is tetrapotassium pyrophosphate ($K_4P_2O_7$).

11. The composition of claim 10, wherein the composition comprises the tin (II) fluoride and tetrapotassium pyrophosphate in a molar ratio of at least 1P:1Sn, wherein P is phosphorous.

12. The composition of claim 10, wherein the composition comprises the tin (II) fluoride and tetrapotassium pyrophosphate in a molar ratio of 1P:1Sn to 15P:1Sn, wherein P is phosphorous.

13. The composition of claim 10, wherein the composition comprises 1 to 10 weight % tin (II) fluoride by weight of the composition and 1 to 40 weight % tetrapotassium pyrophosphate by weight of the composition.

14. The composition of claim 1, wherein the pyrophosphate salt is tetrasodium pyrophosphate ($Na_4P_2O_7$).

15. The composition of claim 14, wherein the composition comprises the tin (II) fluoride and tetrasodium pyrophosphate in a molar ratio of 1P:1Sn to 5P:1Sn, wherein P is phosphorous.

16. The composition of claim 14, wherein the composition comprises 1 to 10 weight % tin (II) fluoride by weight of the composition and 1 to 30 weight % tetrasodium pyrophosphate by weight of the composition.

17. The composition of claim 14, wherein the tin (II) fluoride and tetrasodium pyrophosphate ($Na_4P_2O_7$) form a complex having the formula $[P_2O_7]^{4-}Na^+Sn^{2+}_2F^-$.

18. The composition of claim 1 further comprising another antiperspirant salt comprising a polyvalent cation.

19. The composition of claim 1, wherein the composition is entirely or substantially free of aluminum and optionally zirconium.

20. The composition of claim 1, further comprising a surfactant that is present in an amount of 1 to 30 weight % by weight of the composition, wherein the emollient is present in an amount of 2 weight % by weight of the composition, and wherein the silicone is present in an amount of 2 weight % by weight of the composition.

21. A method to occlude pores and/or reduce sweat in a person in need thereof comprising applying an effective amount of an external personal care composition as claimed in claim 1 to the skin of the person.

* * * * *